United States Patent [19]

Milligan

[11] Patent Number: 4,843,209
[45] Date of Patent: Jun. 27, 1989

[54] METHOD AND APPARATUS FOR LASER STAKING

[75] Inventor: Russ Milligan, Ventura, Calif.

[73] Assignee: Dennis T. Grendahl, Shoreview, Minn.

[21] Appl. No.: 116,874

[22] Filed: Nov. 5, 1987

[51] Int. Cl.[4] .............................................. B23K 26/00
[52] U.S. Cl. .......................... 219/121.63; 219/121.78; 219/121.82; 219/121.73
[58] Field of Search ....................... 219/121.63, 121.64, 219/121.65, 121.66, 121.78, 121.79, 121.82; 128/303.1; 623/6

[56] References Cited

U.S. PATENT DOCUMENTS

| | | | |
|---|---|---|---|
| 3,382,343 | 5/1968 | Muncheryan | 219/121.63 |
| 3,383,491 | 5/1968 | Muncheryan | 219/121.63 |
| 3,517,159 | 6/1970 | Milochevitch | 219/121.63 |
| 3,700,850 | 10/1972 | Lumley et al. | 219/121.82 X |
| 4,358,658 | 11/1982 | Van Blariqan et al. | 219/121.63 |

*Primary Examiner*—C. L. Albritton
*Attorney, Agent, or Firm*—Hugh D. Jaeger

[57] ABSTRACT

Method and apparatus for manual or semiautomatic computer controlled laser staking of a haptic to an optic of an intraocular lens. An Nd:YAG laser with a HeNe laser aiming beam provides laser power to a fiber optic multiplexer to deliver laser energy to a plurality of staking work stations where the haptics are melted or fused to a lens optic. A fiber optic laser stylus is brought in close proximity with a haptic and optic for application of laser power to fuse or join the haptic to the optic in a cylindrically fused fashion, producing no surface wound and effectively sealing the haptic hole.

4 Claims, 5 Drawing Sheets

METHOD AND APPARATUS FOR LASER STAKING

BACKGROUND OF THE INVENTION

1. Field of the Invention

The present invention pertains to an apparatus and method for fusing and staking a haptic to an intraocular lens optic, and more particularly, pertains to a computer controlled YAG laser beam applied to an optic and haptic at a laser work station or switched to a plurality of independent work stations.

2. Description of the Prior Art

The prior art methods of staking a haptic to an optic include a hot needle staking process whereby a heated needle pierces the surface of an optic, where the haptic enters the optic, to produce a small inverted cone shaped wound of about 0.006" diameter and about 0.010" deep to secure the haptic with a single point stake. This produces a blemish on an otherwise perfect surface. The staking hole blemish also provides another irregular surface where undesired bacteria, fungi and debris may be contained. In addition to the problems resulting from the blemish created by the hot piercing needle, loop rotation is another shortcoming of the haptic staking process. Loop rotation occurs as a result of the hot piercing needle striking the haptic not on a tangential point, but to either side of the tangential point, causing the haptic to rotate in the optic hole prior to completion of the melting process, thus causing the haptic to be misaligned with respect to the general plane of the lens optic.

Another problem with heat staking processes is that the heat staking process offers only single point securement of the haptic and optic, leaving an interface gap between the haptic and the optic hole in which the haptic secures, where fungi, bacteria or debris can lodge.

Hot needle staking requires a high degree of skill and, the integrity and quality of prior art devices are subject to the proficiency level of the operator.

The present invention overcomes the disadvantages of the prior art by providing a computer assisted non-contact YAG laser staking system for fusing of a haptic to a lens optic.

SUMMARY OF THE INVENTION

The general purpose of the present invention is to provide a method and apparatus for a computer controlled laser staking where a 50 watt continuous wave Nd:YAG laser, operating at a frequency in the range of 1.064 microns, is coupled into a fiber optic multiplexer controller with a HeNe aiming laser which can be switched into a plurality of fiber optic cables. The fiber optic cables are routed to individual semiautomatic staking work stations. The fiber optic multiplexer controller and laser are computer controlled.

The staking process, utilizing the above-described system, produces a stake that melts the haptic and optic together internally to produce a cylindrical bond. A fiber optic laser stylus at the staking work station operates in close proximity to the lens optic surface, but does not contact the optic surface, thereby avoiding the chance of any blemish due to a mechanical contact. The non-contact operational aspect also has the advantage of greatly reducing or eliminating haptic tip rotation which has been a continuing problem with other staking processes. When the haptic is lased, the haptic material, such as PMMA, swells. This swelling, in combination with the internal melting or fusion, effectively seals a majority of the haptic hole to greatly reduce the potential of bio-burden or internal contamination.

According to one embodiment of the present invention, there is provided a laser staking system where a control computer coordinates an Nd:YAG laser and a HeNe aiming laser with a fiber optic multiplexer controller to send laser energy through fiber optic lines to a plurality of independent laser staking work stations. Each laser work station includes a base, an x-y axis positioning table with micrometer adjusters, brackets on the x-y axis positioning table for clamping a carousel fixture to the x-y positioning table, a vertical central post for mounting of vertically adjustable upper and lower clamp bases, a slide mounted laser arm mounted to the lower clamp base, a pneumatic actuating cylinder affixed to the upper clamp base to vertically position the laser arm, a fiber optic laser stylus affixed to the vertically positionable laser arm, an L bracket attached to a slide mechanism upon which the laser arm is mounted, a rod attached to the slide mechanism which contacts a depth stop microcomputer and a switch which is operated by the L bracket.

One significant aspect and feature of the present invention is an intraocular lens laser staker having a computer controlled Nd:YAG laser with a HeNe aiming laser which feeds a fiber optic multiplexer controller.

Another significant aspect and feature of the present invention is an intraocular lens laser staker having fiber optic multiplexer controller to feed a plurality of work stations.

Another significant aspect and feature of the present invention is the use of a laser beam fired through a fiber optic laser stylus to fuse a haptic to an optic of an intraocular lens.

Yet another significant aspect and feature of the present invention is a staking work station wherein a fiber optic laser stylus applies laser energy to an optic lens and haptic affixed in a lens carousel after a low energy laser is used to align the laser beam with respect to the optic and haptic.

Still another significant aspect and feature of the present invention is staking of a haptic and an optic without creating blemishes or surface wounds.

A further significant aspect and feature of the present invention is a staking where high mechanical strength is obtained through melt fusing or bonding over the cylindrical area of abutting haptic and the optic surfaces.

Still a further significant aspect and feature of the present invention is the fusing of the haptic in the hole of the optic to effectively seal the optic hole.

Yet a further significant aspect and feature of the present invention is an intraocular lens with a reduced bio-burden capability.

Still another significant aspect and feature of the present invention is the greatly reduced possibility of haptic rotation in the optic hole during staking.

Having thus described the embodiments of the present invention, it is a principal object hereof to provide a method and apparatus for laser staking.

One object of the present invention is to provide a semi-automatic computer assisted system for laser staking at a number of laser work stations.

Another object of the present invention is to provide a greatly improved method of haptic bonding.

DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
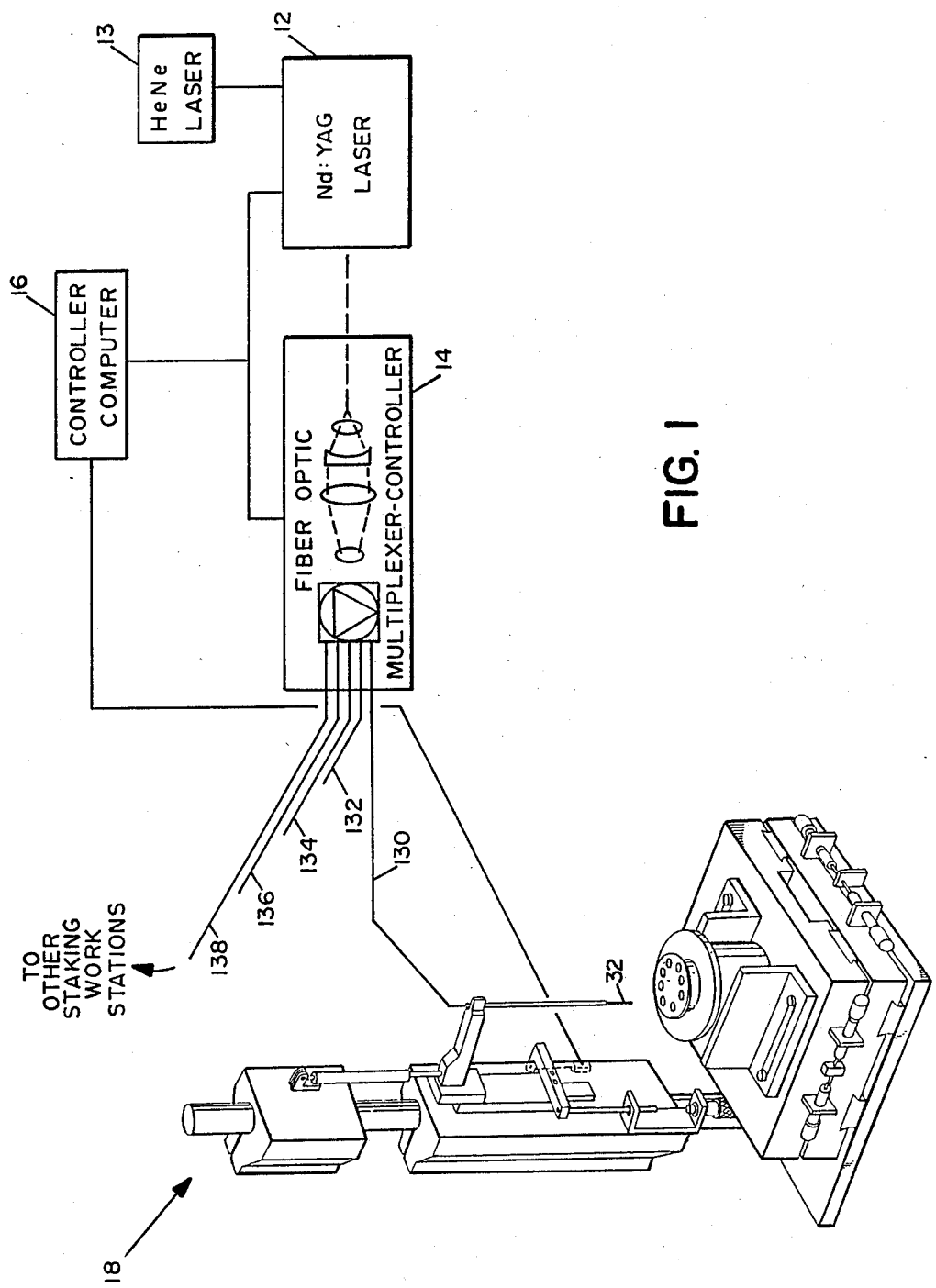
FIG. 1 illustrates a schematic drawing of the laser staking system.

FIG. 1 illustrates a laser staking system 10 for the staking or joining of a lens haptic to an intraocular lens optic. The system includes a continuous wave Nd:YAG heating laser 12, having an optically pumped Nd:YAG crystal as its active lasing component, such as a Quantronix model 116; a HeNe aiming laser 13; a fiber optic multiplexer controller 14, such as a Robolase Systems Octopus; which is electro-optically switched by a control computer 16, such as an IBM 5745; and a laser staking work station 18.

Figure 2:
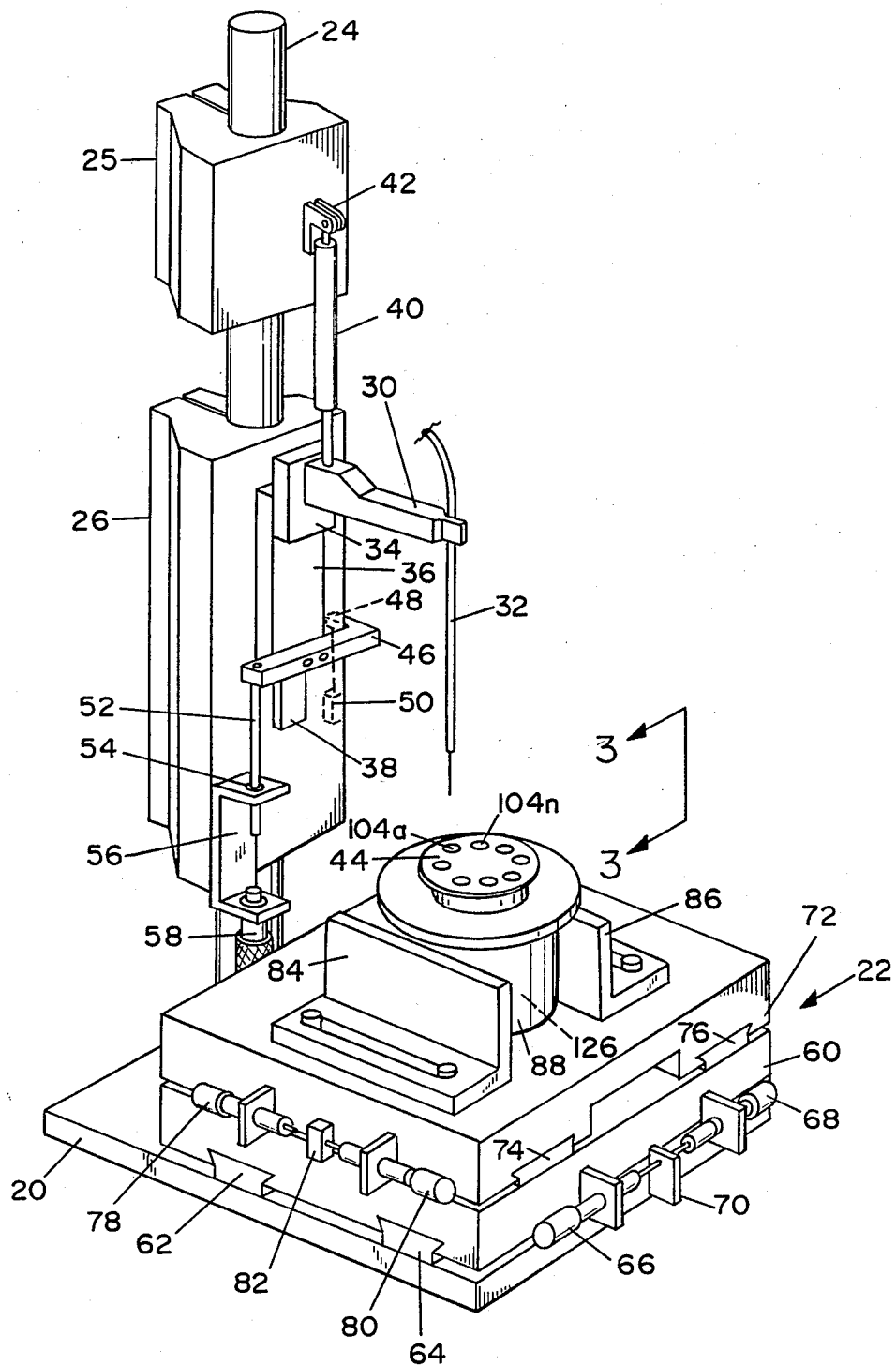
FIG. 2 illustrates an isometric view of a staking work station.

FIG. 2 illustrates an isometric view of the work station 18 which is used to accurately position the optic and haptic in a target area and bring the terminating end of the laser fiber into position for staking. The work station includes a base 20, an x-y axis positioning table 22, a support post 24, an upper clamp base 25, and a lower clamp base 26 affixed over the support post 24. A stylus support arm 30, holding a fiber optic laser stylus 32, is affixed to a mounting bracket 34. Mounting bracket 34 is attached to a vertical slide bar 36 which slides over and along a vertically oriented bar guide 38 secured to the lower clamp base 26.

A pneumatic cylinder 40, attached between the stylus support arm 30 and a bracket 42 on the upper clamp base 25, drives the stylus support arm 30 and the fiber optic laser stylus 32 vertically until it is juxtaposed to a lens and a haptic in the carousel fixture 44 mounted in the x-y axis positioning table 22. An L bracket 46, secured to the vertical slide bar 36, includes an L bracket extension 48, shown in dashed lines, which actuates a switch 50, also shown in dashed lines. A rod 52 extends vertically from the L bracket 46, through a hole 54 in a guide bracket 56, to contact a micrometer depth gauge 58 also mounted in the guide bracket 56 for precise vertical control of the fiber optic laser stylus 32. The stylus 32 stylus support arm 30, mounting bracket 34, L bracket 46 and rod 52 descend as a unit to ensure exact vertical positioning of the fiber optic laser stylus 32 with respect to an optic and a haptic in the carousel fixture 44.

The x-y axis positioning table 22 includes an x-motion plate 60 which slides along base 20 and mounted slide rails 62 and 64. Micrometer adjusters 66 and 68 mount on the x-motion plate 60 to adjust against a base mounted vertically oriented tab 70 to position the x-motion plate 60 along the x-axis. Similarly, a y-motion plate 72 slides along x-motion plate 60 and on slide rails 74 and 76. Micrometer adjusters 78 and 80, mounted on the y-motion plate 72, adjust against x-motion plate 60 and mounted tab 82 to position the y-motion plate 72 along the y-axis. Adjustable L brackets 84 and 86, on the upper surface of y-motion plate 72, secure the carousel fixture body 88 to the x-y axis positioning table 22.

Figure 3:
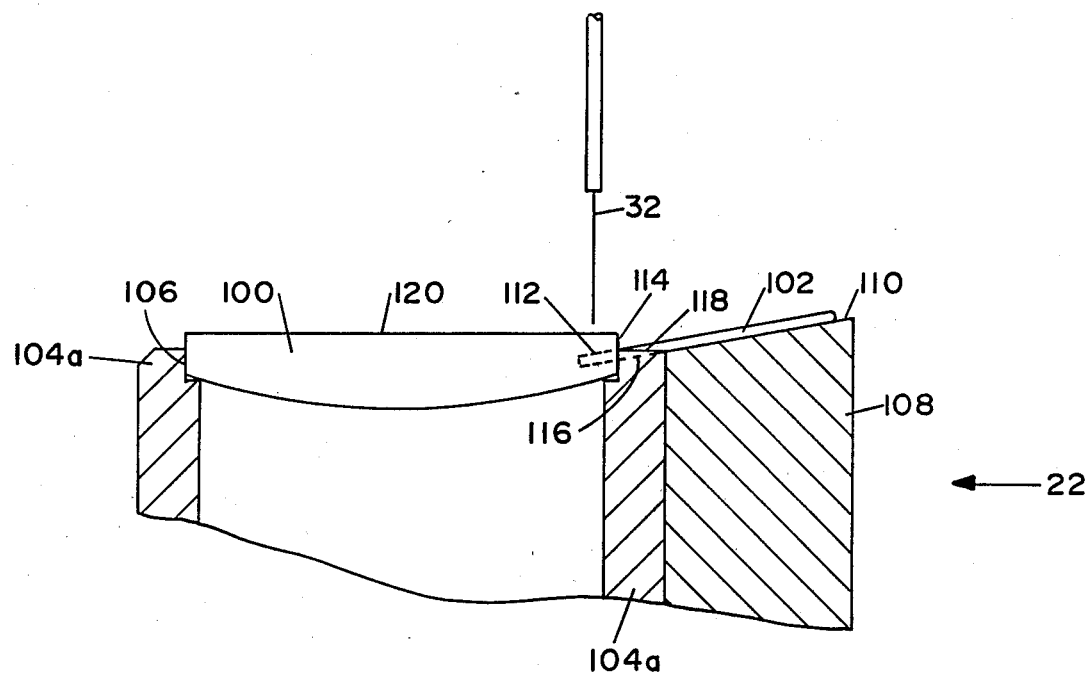
FIG. 3 illustrates a cross-sectional view taken along line 3—3 of FIG. 2 showing an optic and a haptic in a carousel fixture.

FIG. 3 illustrates a cross-sectional view taken along line 3—3 of FIG. 2 to show a lens 100 and a haptic 102 held in the carousel fixture 44 for lasing. The carousel fixture 44, as also illustrated in FIG. 2, includes a plurality of fixtures 104a–104n for holding lenses and haptics located on the carousel fixture 44. Carousel fixture 44 rotates about a vertical axis to sequentially position the optics in each of the optic fixtures 104a–104n beneath the fiber optic laser stylus 32 for lasing. The optic fixture 104a includes an annular optic seat 106 in the upper region of the cylindrically shaped optical fixture 104a. The optical fixture 104a is secured to a haptic loop fixture 108 which includes an upper surface 110 for positioning and aligning a haptic 102 with a haptic hole 112 in the edge 114 of the optic 100. The upper surface 110 may be angled with respect to the horizontal plane to provide for positive or negative vaulting of the haptic 102, or it can be horizontally aligned to position the loop haptic 102 in a horizontal plane for a non-vaulted loop. A groove 116 is located in the upper surface 118 of the haptic loop fixture 108 for accommodation of the haptic 102. The fiber optic laser stylus 32 is illustrated ready for lasing and juxtaposed to the posterior surface 120 of the optic 100 and over the haptic hole 112 which has the haptic 102 engaged therein.

Figure 4:
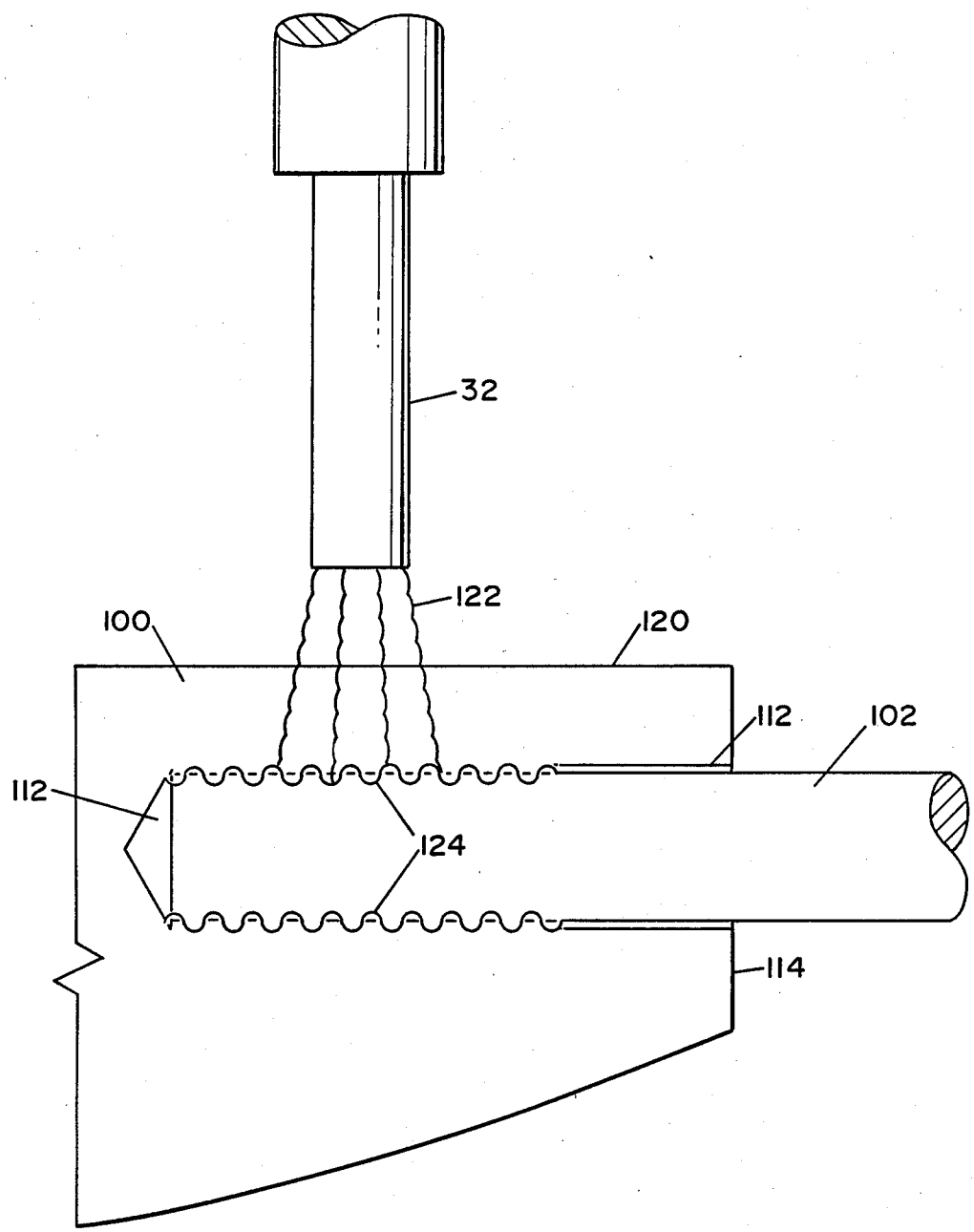
FIG. 4 illustrates a haptic being lased to an optic.

FIG. 4 illustrates a haptic 102 being lased into haptic hole 112 of the optic 100 where all numerals correspond to those elements previously described. A laser beam 122, emitted from the fiber optic laser stylus 32, penetrates the lens optic 100 to heat both the end portion of the haptic 102 engaged in haptic hole 112 and the cylindrical surfaces of the haptic hole 112 to fuse and unite the outer cylindrical surface of the haptic 102 to the cylindrical surfaces of haptic hole 112. The area of fusion 124 is illustrated by lines in the drawing. Heat is transmitted and distributed along the area of fusion 124 by a conductive wave guide effect, whereby heat is transferred along the loop in the hole and radiates away from the actual laser spot. As the haptic 102 is lased, the haptic material within the optic 100 swells. This, in combination with the internal fusion and melting, effectively seals a majority of the haptic hole 112 to produce an intraocular lens with reduced potential of bio-burden. The optic 100 does not melt because the PMMA material is 95% transparent to YAG laser as long as the power density does not exceed the plastics threshold temperature. This is accomplished by balancing the amount of laser energy used, with the time of exposure. Since the inside of the haptic hole 112 and the haptic 102 itself absorbs energy quicker than the lens surface, the haptic 102 melts first, sparing the lens surface. A pigmented haptic loop which will absorb more laser energy and fuses or heats faster can also be used.

Figure 5:
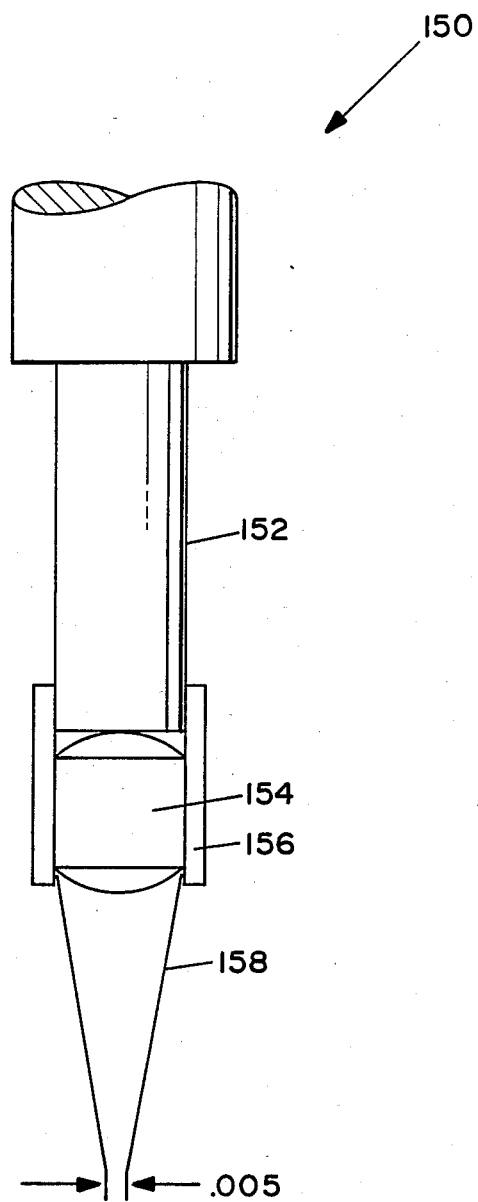
FIG. 5 illustrates an alternative embodiment of a focused beam lasing system.

FIG. 5 illustrates an alternative embodiment of a focused beam lasing system 150 where a laser beam emitted from a fiber optic laser stylus 152 is focused by a micro-optic 154 in a housing 156 which focuses and concentrates the laser beam 158 in approximately a 0.005 inch spot size in a focal length of four millimeters. The size of the micro-optic can be approximately 0.040 inches in diameter and approximately 0.080 to 0.100 inches long.

MODE OF OPERATION

The mode of operation is best explained with reference to FIGS. 1, 2, and 3. A system operator places an optic 100 and a haptic 102 into the optic fixture 104a and into the haptic loop fixture 108, respectively, of the carousel fixture 44. After loading, the operator locks the carousel fixture body 88 between L brackets 84 and 86 on the x-y axis positioning table 22.

Prealignment for automatic or semi-automatic operation is accomplished as follows: The stylus support arm 30, holding the fiber optic laser stylus 32, is roughly positioned above the posterior surface 120 of the optic 100 by the pneumatic cylinder 40. The optic 100 is then positioned by micrometer adjusters 66, 68, 78 and 80 at a respective x-y axis. The beam to be subsequentially transmitted is aimed by a visible red beam of an HeNe aiming laser 13 over the region to be heated. When proper alignment of the HeNe aiming beam has been achieved, the fiber optic laser stylus 32 is fine adjusted in the z axis to the optimum distance above the posterior surface 120 of the optic overlying the haptic hole 112 with the haptic 102 end. The adjustment is made by the micrometer depth gauge 58. Once the fiber optic laser stylus is properly positioned along the x, y and z axis, the length of time and power setting for the laser exposure, such as 25 watts of power for 1.5 seconds, is selected and inputted via the control computer 16. This completes the alignment procedure.

The actual staking operator enters the appropriate command into the control computer 16 which then causes pneumatic cylinder 40 to lower the stylus support arm 30 to its prealigned position. When stylus support arm 30 reaches final position, it closes triggering switch 50, generating a signal to the computer. This signal causes the control operator to issue a command to the laser system to fire through the fiber optic laser stylus 32 for the prescribed amount of time at the selected power level lasing haptic 102 to the optic 100 as previously described. The stylus support arm 30 then retracts. The carousel fixture 44 is then rotated manually or automatically by means of a carousel actuator 126 in the carousel fixture body 88 to position the next optic for lasing.

The fiber optic multiplexer controller 14 is aligned with the output beams of the HeNe aiming laser 13 and the Nd:YAG heating laser 12. The output of the Nd:YAG laser 12 is coupled into the fiber optic multiplexer controller 14 where it is divided and fed into multiple fiber optic lines 130, 132, 134, 136 and 138, as illustrated in FIG. 1, which deliver laser output to a plurality of work stations. Any appropriate number of fiber optic lines may deliver laser power to any appropriate member of work stations similar to work station 18. The laser energy exiting the fiber may then be either focused or left unfocused depending upon the application. As previously and briefly describe, a HeNe aiming laser 13 is integrated into the YAG laser as an aiming beam to produce a brilliant red light which is coincidental to the YAG beam. When the system is activated, the red HeNe aiming laser 13 light indicates where invisible YAG energy rays would strike the optic 100.

Various modifications can be made to the present invention without departing from the apparent scope thereof.

I claim:
1. A staking work station comprising:
   a. a base;
   b. an x-y axis positioning table affixed to said base;
   c. a carousel fixture affixed to said x-y axis positioning table;
   d. a vertical support post affixed to said base;
   e. an adjustable lower clamp base attached to said support post;
   f. a slide bar attached to said lower clamp base;
   g. a laser stylus attached to said slide bar;
   h. a pneumatic actuator attached to said vertical support post and said slide bar to move said laser stylus relative to said fixture; and,
   i. switch means actuated by said slide bar when said laser stylus reaches a predetermined position relative to said carousel.
2. Staking work station of claim 1 including the use of Nd:YAG laser to affix a haptic to an optic of an intraocular lens.
3. Staking work station of claim 1 including the use of a Nd:YSG laser focused and concentrated through a micro-optic to affix a haptic to an optic of an intraocular lens.
4. A laser staking work station comprising:
   a. a base;
   b. an x-y axis positioning table on said base including x-y positioning micrometers adjusters;
   c. brackets on said s-y axis positioning table for clamping a carousel fixture to said x-y positioning table;
   d. a vertical post mounted centrally on said base for mounting of vertically adjustable upper and lower clamp bases;
   e. a slide mounted laser arm mounted on said lower clamp base;
   f. a pneumatic actuating cylinder affixed to said upper clamp base for vertically positioning of a vertically positionable laser arm and a fiber optic laser stylus affixed to a slide bar;
   g. an L bracket attached to said slide bar;
   h. a rod attached to said slide bar which contacts a depth stop micrometer; and,
   i. a switch attached to said lower clamp base which is actuated by said L bracket to activate YAG laser beam.

* * * * *